United States Patent
Moua et al.

(10) Patent No.: US 8,808,283 B2
(45) Date of Patent: Aug. 19, 2014

(54) INDUCTIVE POWERED SURGICAL DEVICE WITH WIRELESS CONTROL

(75) Inventors: Tony Moua, Broomfield, CO (US); Jason L. Craig, Loveland, CO (US)

(73) Assignee: Covidien LP, Mansfield, MA (US)

( * ) Notice: Subject to any disclaimer, the term of this patent is extended or adjusted under 35 U.S.C. 154(b) by 1085 days.

(21) Appl. No.: 12/827,783

(22) Filed: Jun. 30, 2010

(65) Prior Publication Data
US 2012/0004652 A1 Jan. 5, 2012

(51) Int. Cl.
*A61B 18/18* (2006.01)
(52) U.S. Cl.
USPC .............................................. 606/41; 606/32
(58) Field of Classification Search
USPC .................................. 606/32, 33, 41; 607/65
See application file for complete search history.

(56) References Cited

U.S. PATENT DOCUMENTS

| | | | |
|---|---|---|---|
| 5,999,061 A | 12/1999 | Pope et al. | |
| 7,379,775 B2 * | 5/2008 | Parramon et al. | 607/61 |
| 2003/0229381 A1 * | 12/2003 | Hochmair et al. | 607/57 |
| 2007/0060919 A1 | 3/2007 | Isaacson et al. | |
| 2008/0227424 A1 | 9/2008 | Muhammad et al. | |
| 2008/0281322 A1 * | 11/2008 | Sherman et al. | 606/42 |
| 2011/0009856 A1 * | 1/2011 | Jorgensen et al. | 606/33 |
| 2011/0208179 A1 * | 8/2011 | Prakash et al. | 606/33 |
| 2011/0213354 A1 * | 9/2011 | Smith | 606/33 |
| 2011/0217923 A1 * | 9/2011 | Ma | 455/39 |
| 2011/0224665 A1 * | 9/2011 | Crosby et al. | 606/33 |
| 2011/0278948 A1 * | 11/2011 | Forsell | 307/104 |
| 2012/0116380 A1 * | 5/2012 | Madan et al. | 606/33 |
| 2013/0261616 A1 * | 10/2013 | Prakash et al. | 606/33 |

FOREIGN PATENT DOCUMENTS

WO   WO 2008/003058   1/2008

* cited by examiner

*Primary Examiner* — Linda Dvorak
*Assistant Examiner* — Jocelyn D Ram

(57) ABSTRACT

A system and method for wirelessly powering an electrosurgical device using a generator to generate a radio frequency (RF) energy field. A switch on the electrosurgical device sends a wireless signal to the generator, where the generator allows a current to pass through an inductive coil to generate the RF energy field. The RF energy field induces a current to flow across an inductive coil within the electrosurgical device. The current flow is then processed through a RF conditioning circuit and outputted to the end effector assembly of the device.

12 Claims, 7 Drawing Sheets

INDUCTIVE POWERED SURGICAL DEVICE WITH WIRELESS CONTROL

BACKGROUND

1. Technical Field

The present disclosure relates to apparatuses and method for wirelessly supplying energy to a surgical device, and more particularly, to an inductive RF generator for supplying energy to a wireless surgical device.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. In monopolar electrosurgery, as shown in FIG. 1A, a source or active electrode 2 delivers radio frequency energy from the electrosurgical generator 20 to the tissue and a return electrode 6 carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In bipolar electrosurgery, as shown in FIG. 1B, one of the electrodes of the hand-held instrument functions as the active electrode 14 and the other as the return electrode 16. The return electrode is placed in close proximity to the active electrode such that an electrical circuit is formed between the two electrodes (e.g., electrosurgical forceps 10). In this manner, the applied electrical current is limited to the body tissue positioned immediately adjacent to the electrodes. When the electrodes are sufficiently separated from one another, the electrical circuit is open and thus inadvertent contact with body tissue with either of the separated electrodes does not cause current to flow.

Electrosurgical instruments have become widely used by surgeons in recent years. By and large, most electrosurgical instruments are hand-held instruments, e.g., an electrosurgical pencil, which transfer radio-frequency (RF) electrical or electrosurgical energy to a tissue site. As used herein the term "electrosurgical pencil" is intended to include instruments which have a handpiece that is attached to an active electrode and which is used to cauterize, coagulate and/or cut tissue. Typically, the electrosurgical pencil may be operated by a handswitch or a foot switch. The active electrode is an electrically conducting element that is usually elongated and may be in the form of a thin flat blade with a pointed or rounded distal end. Alternatively, the active electrode may include an elongated narrow cylindrical needle that is solid or hollow with a flat, rounded, pointed or slanted distal end. Typically electrodes of this sort are known in the art as "blade", "loop" or "snare", "needle" or "ball" electrodes.

As mentioned above, the handpiece of the electrosurgical pencil is connected to a suitable electrosurgical energy source (i.e., generator) which produces the radio-frequency electrical energy necessary for the operation of the electrosurgical pencil. In general, when an operation is performed on a patient with an electrosurgical pencil, electrical energy from the electrosurgical generator is conducted through the active electrode to the tissue at the site of the operation and then through the patient to a return electrode. The return electrode is typically placed at a convenient place on the patient's body and is attached to the generator by a conductive material.

Some electrosurgical procedures utilize electrosurgical forceps that use both mechanical clamping action and electrical energy to affect hemostasis by heating tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic instruments are typically inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas. Such endoscopic instruments may use monopolar forceps, bipolar forceps or a combination monopolar/bipolar forceps.

Generators have a fixed number of inputs for connecting surgical devices using cables. The use of many cables can cause entanglement of the cables as the surgeon performs the surgery. Additionally, the cables used to connect the surgical devices have substantial weight, where the substantial weight of the cable can cause strain on the surgeon during long surgeries.

SUMMARY

In accordance with the present disclosure, a system and method for wirelessly powering an electrosurgical device using a generator to generate a radio frequency (RF) energy field. A switch on the electrosurgical device sends a wireless signal to the generator, where the generator allows a current to pass through an inductive coil to generate the RF energy field. The RF energy field induces a current to flow across an inductive coil within the electrosurgical device. The current flow is then processed though a RF conditioning circuit and outputted to the end effector assembly of the device.

According to an embodiment of the present disclosure, a method for wirelessly operating a hand held electrosurgical device includes the steps of selecting a switch on the hand held electrosurgical device and sending an instruction wirelessly to a generator to generate an RF energy field. The method further includes the steps of generating the RF energy field and the RF energy field inducing a current across an inductor within the hand held device that causes a RF signal. The method also includes the step of supplying the RF signal to an end effector assembly to perform a surgical procedure.

According to another embodiment of the present disclosure, a system for wirelessly operating a hand held electrosurgical device. The system includes a generator and a hand held electrosurgical device. The generator includes a power source and a first inductor to generate a RF energy field. The hand held electrosurgical device includes a second inductor, a power board, a wireless communication board, a control interface, and an end effector assembly. The control interface includes at least one switch and is configured to send a first message to the wireless communication board when the at least one switch is selected. The wireless communication board, in response to receiving the first message from the control interface, sends a second message to the generator instructing the generator to generate the RF energy field. The power board receives a RF signal from the second inductor when the RF energy field induces a current across the second inductor, and sends the RF signal to the end effector.

According to another embodiment of the present disclosure, a method for wirelessly operating a hand held electrosurgical device includes the steps of generating a RF energy field and selecting a switch on the device to select a mode of operation. The RF energy field induces a current across an inductor within the device that causes a RF signal. The method further includes the steps of conditioning the RF signal into the selected mode, and supplying the conditioned RF signal to an end effector assembly to perform a surgical procedure.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1A:
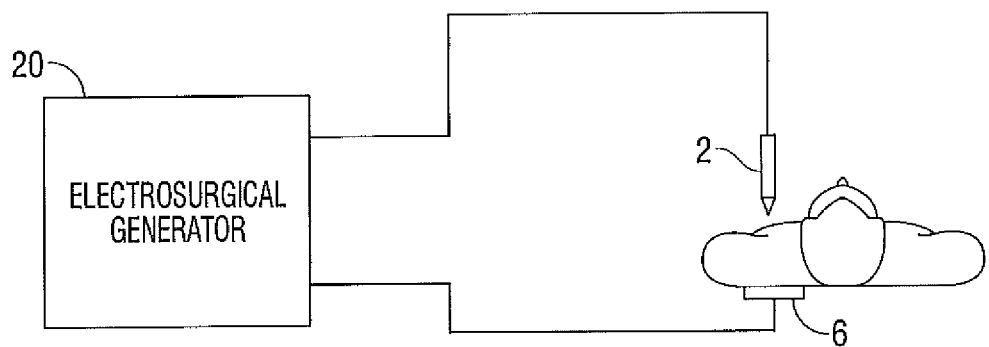
FIGS. 1A-1B are schematic diagrams of electrosurgical systems.
Figure 1B:
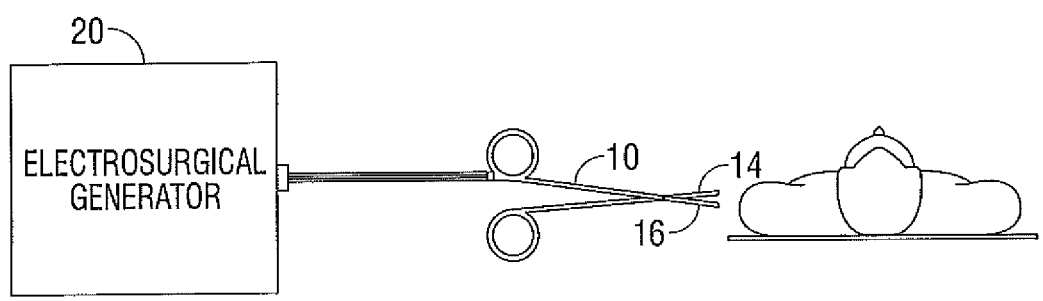

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Electromagnetic energy is generally classified by increasing energy or decreasing wavelength into radio waves, microwaves, infrared, visible light, ultraviolet, X-rays and gamma-rays. As used herein, the tem "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As used herein, the term "RF" generally refers to electromagnetic waves having a lower frequency than microwaves.

Figure 2:
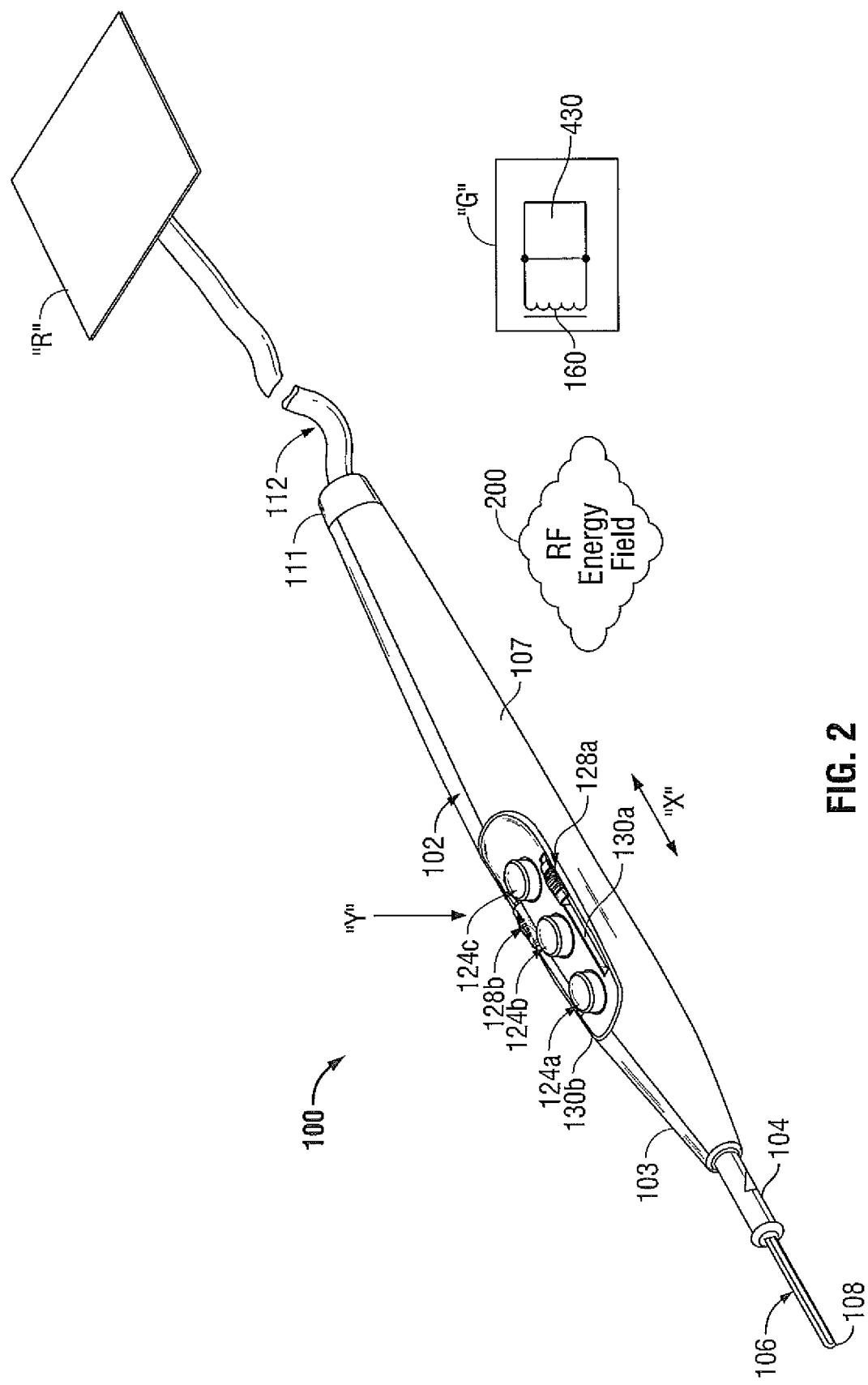
FIG. 2 is a perspective view of an electrosurgical pencil and generator in accordance with an embodiment of the present disclosure.
Figure 3:
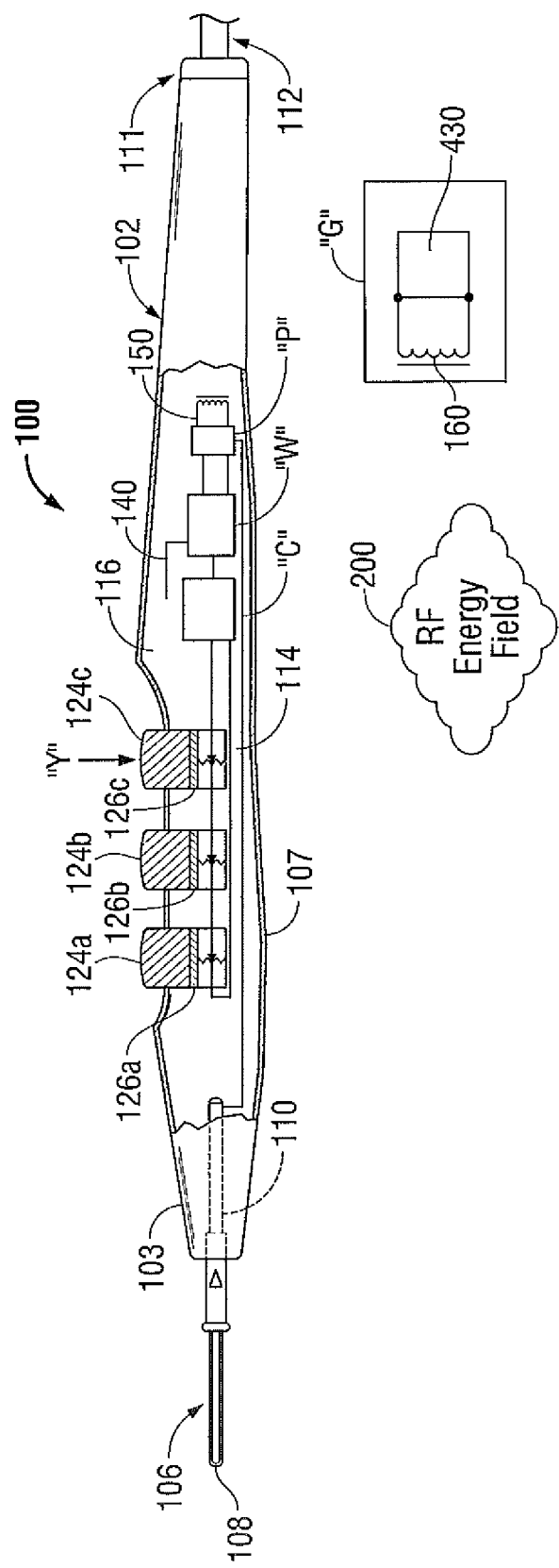
FIG. 3 is a partially broken away, side elevational view of the electrosurgical pencil of FIG. 2.

FIGS. 2-3 show an electrosurgical pencil constructed in accordance with an embodiment of the present disclosure is shown generally as 100. Electrosurgical pencil 100 includes an elongated housing 102 configured and adapted to support a blade receptacle 104 at a distal end 103 thereof which, in turn, receives a replaceable electrocautery end effector 106 in the form of a loop and/or blade therein. Electrocautery blade 106 is understood to include a planar blade, a loop, a needle and the like. A distal end portion 108 of blade 106 extends distally from receptacle 104 while a proximal end portion 110 of blade 106 is retained within distal end 103 of housing 102. Electrocautery blade 106 may be fabricated from a conductive type material, such as, for example, stainless steel, or is coated with an electrically conductive material. The electrosurgical pencil also includes a power board "P", a wireless communication board "W", and a controller board "C".

As shown, electrosurgical pencil 100 is coupled to a return pad "R" via a cable 112. Cable 112 includes a transmission wire which electrically interconnects return pad "R" with return port 111 of electrosurgical pencil 100. Alternatively, the return pad "R" can be connected to the generator "G".

For the purposes herein, the terms "switch" or "switches" includes electrical actuators, mechanical actuators, electromechanical actuators (rotatable actuators, pivotable actuators, toggle-like actuators, buttons, etc.) or optical actuators.

Electrosurgical pencil 100 includes at least one activation switch, e.g., three activation switches 124a-124c, each of which are supported on an outer surface 107 of housing 102. Each activation switch 124a-124c is operatively connected to a respective switch 126a-126c which, in turn, controls the transmission of RF electrical energy supplied from a power board "P" and an electrosurgical generator "G" to electrosurgical blade 106. More particularly, switches 126a-126c are electrically coupled to control loop 116 and are configured to close and/or complete control loop 116, which causes the controller board "C" to send an instruction to the wireless communication board "W". The wireless communication board "W" sends a wireless signal using antenna 140 to the electrosurgical generator "G" to generate an RF energy field 200. The RF energy field 200 causes a current to flow though an inductor 150 connected to power board "P". As the current flows through inductor 150, energy is transmitted to electrocautery blade 106 via a wire 114 to perform a surgical operation.

In an alternative embodiment, the RF energy field 200 can be continuously in an "on" mode by selecting a switch on the electrosurgical device 100 or on the electrosurgical generator "G". Additionally, switches 124a-124c can be used to supply energy in an operational mode selected by the user without sending information to the electrosurgical generator "G", where the power board "P" conditions the RF signal from inductor 150 into the selected operational mode. The operational mode can be cut, ablate, coagulate, or seal depending on the surgical instrument being employed.

Electrosurgical pencil 100 further includes one or more intensity controllers 128a and/or 128b, each of which are slidingly supported in guide channels 130a, 130b, respectively, which are formed in outer surface 107 of housing 102. Each intensity controller 128a and 128b is a slide-like potentiometer. Each intensity controller 128a and 128b and respective guide channel 130a and 130b may be provided with a series of cooperating discreet or detented positions defining a series of positions to allow easy selection of output intensity from a minimum amount to a maximum amount. The series of cooperating discreet or detented positions also provide the surgeon with a degree of tactile feedback. One of the series of positions for intensity controllers 128a, 128b may be an "off" position (i.e., no level of electrical or RF energy is being transmitted).

Intensity controllers 128a and 128b are configured and adapted to adjust one of the power parameters (e.g., RF energy field, voltage, power and/or current intensity) and/or the power verses impedance curve shape to affect the perceived output intensity.

As shown in FIG. 3, electrosurgical pencil 100 may include a controller board "C", a wireless communication board "W", and a power board "P" within housing 102. Controller board "C" receives inputs from the various switches, intensity controller, nubs, potentiometers or the like that may be disposed in housing 102 and outputs a signal to wireless communication board "W" that, in turn, sends a wireless signal through antenna 140 to the generator "G" to generate RF energy field 200 from a generator side inductor 160 connected to a power source 430. An inductor 150 is connected to a power board "P", and the RF energy field 200 induces a current to flow through inductor 150. The power board "P" then sends an energy signal to electrosurgical blade 106. The type of energy signal sent to the electrosurgical blade 106 may be controlled through the controller board "C" using switches 124a-124c and/or 128a-128b.

Alternatively, the electrosurgical pencil 100 may include a rechargeable battery (not shown). The battery may be recharged when RF field 200 induces a current to flow through inductor 150. The battery then supplies the energy signal through the power board "P" to the electrosurgical blade 106.

In another embodiment, the electrosurgical pencil 100 may include a capacitor (not shown). The capacitor may be charged when RF field 200 induces a current to flow through inductor 150. The capacitor then supplies the energy signal through the power board "P" to the electrosurgical blade 106. For example, the capacitor may take 20 seconds to charge and provide a 20 second burst of electrical energy to the power board "P" to supply to the electrosurgical blade 106. The capacitor may have a capacitance between about 1 mF and 20 F.

Figure 4:
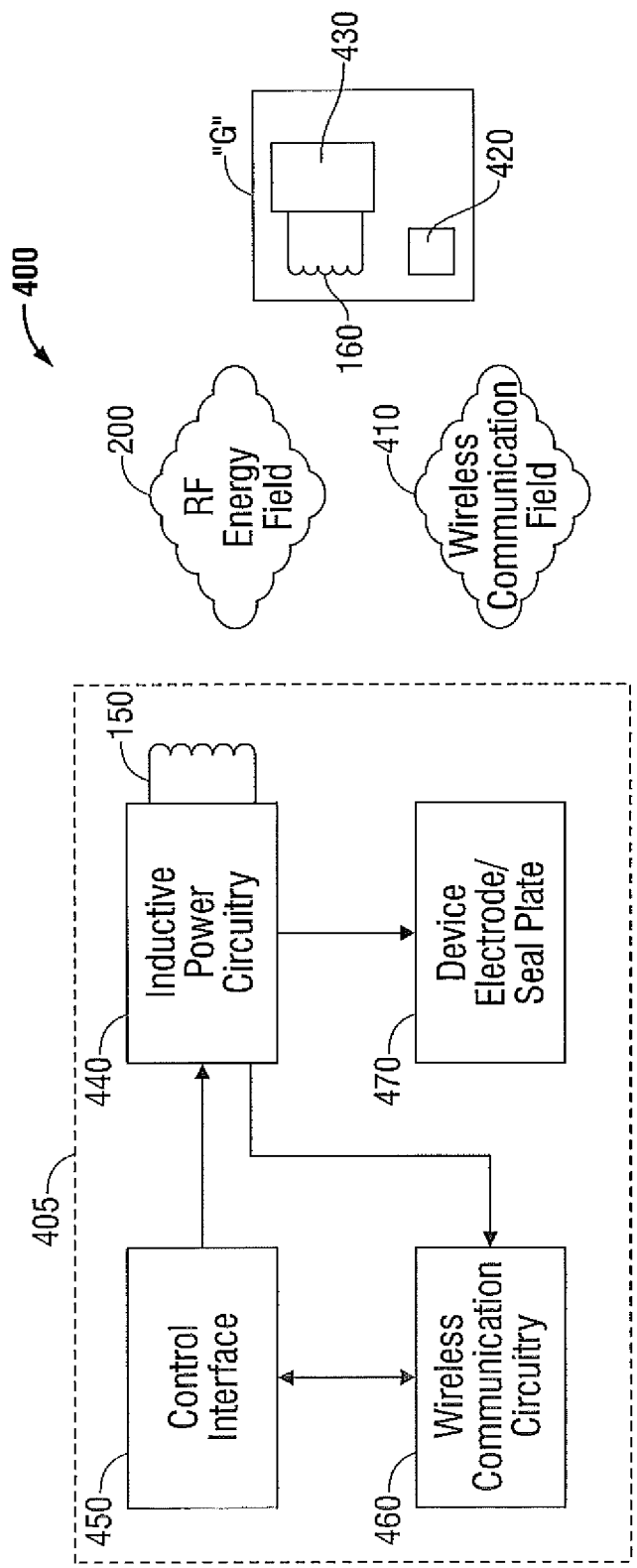
FIG. 4 is a schematic diagram of a wireless RF system according to an embodiment of the present disclosure.
Figure 5A:
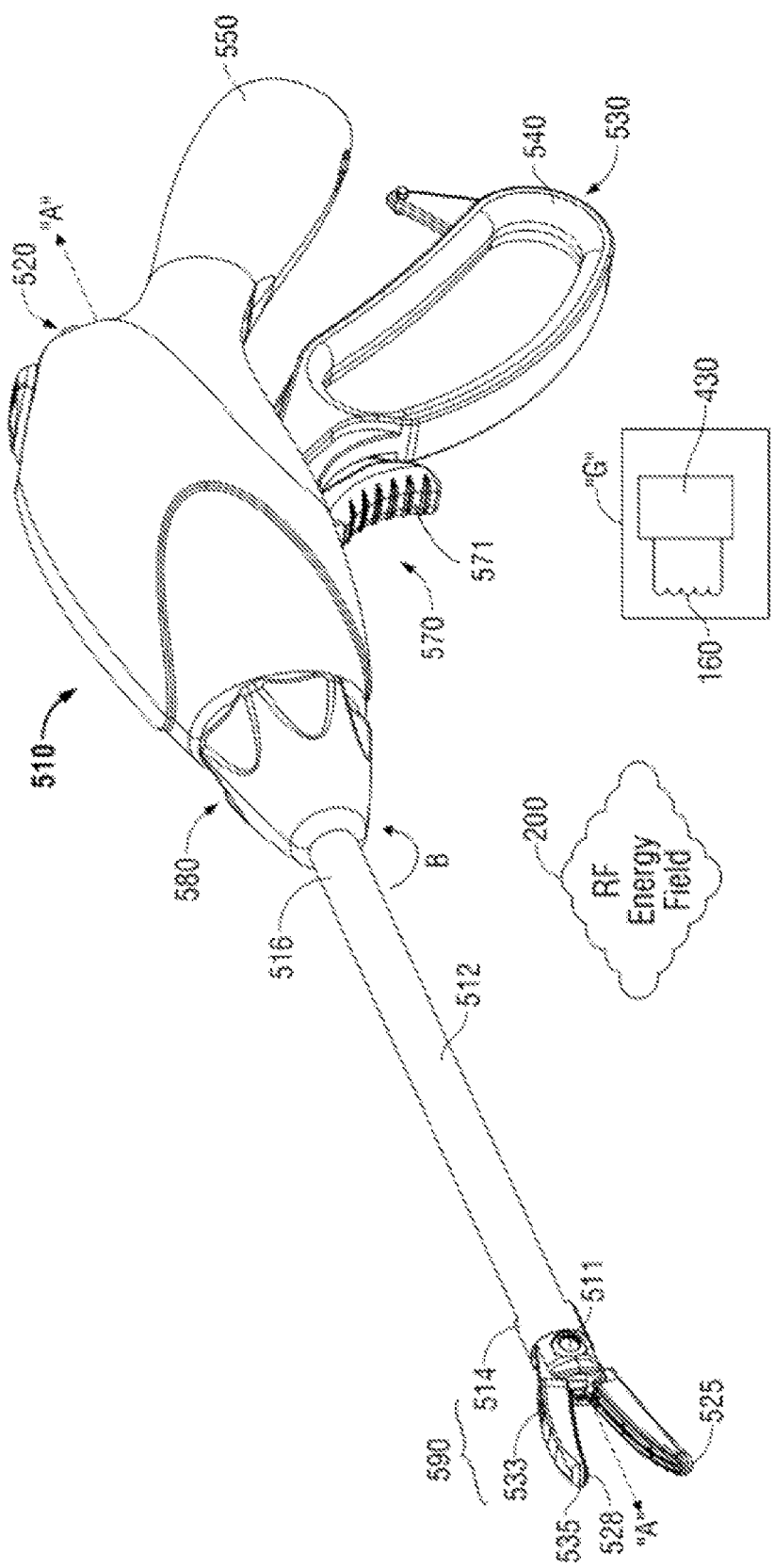
FIG. 5A is a perspective view of an endoscopic forceps and generator according to the present disclosure.

FIG. 4 discloses a schematic of a wireless RF system 400 to power an electrosurgical device 100 or 510 (see FIGS. 2 and 5a, respectively). An electrosurgical device 405, such as electrosurgical device 100 or 510, includes a control interface 450, inductive power circuitry 440, an inductor 150, wireless communication circuitry 460, and/or a device electrode or seal plate 470.

A generator "G" includes at least an inductor 160 connected to a power source 430. The inductor 160 may be a single inductor with an inductance between about 0.33 µH and 3.3 µH. Alternatively, inductor 160 may be two or more inductors connected in series or parallel. The inductor 160 generates an RF energy field 200, where the size of the field is calculated according to Faraday's Law of induction. The RF energy field 200 causes a current to flow through inductor 150. The inductor 150 is connected to inductive power circuitry 440, where the inductive power circuitry filters and/or conditions the RF signal. The RF signal may be conditioned based on the selected mode. The RF signal is then sent to the electrode 106 (See FIG. 2) or seal plate 528 (See FIG. 5a) of the device.

The control interface 450 is an interface between an operator and the device 405. The control interface 450 includes one or more switches, such as switches 124a-124c, that allow the operator to select the mode for operating the device 405. The control interface 450 is connected to the wireless communication circuitry 460. The wireless communication circuitry 460 relays the mode selected from the control interface 450 over the wireless communication field 410 to data port 420 in the generator "G". The generator "G" then operates in the mode selected by the operator. The mode may be continuously on, selectably on, cut, seal, ablate, or coagulate. For example, the generator "G" may provide a RF field 200 with a pulsed waveform, when the surgeon is sealing tissue with the device 100. Alternatively, the generator "G" generates the RF Field 200, and the power circuitry 440 conditions an RF signal from the inductor 150 into a pulsed waveform for sealing tissue. The wireless communication board 460 replaces the signal wires needed in the prior art to communicate with the generator "G". The wireless communication circuitry 460 may include a battery (not shown) to allow the wireless communication circuitry to send a signal to the generator "G" before the generator "G" generates the RF field 200 that induces power in the inductive power circuitry 440.

Figure 5B:
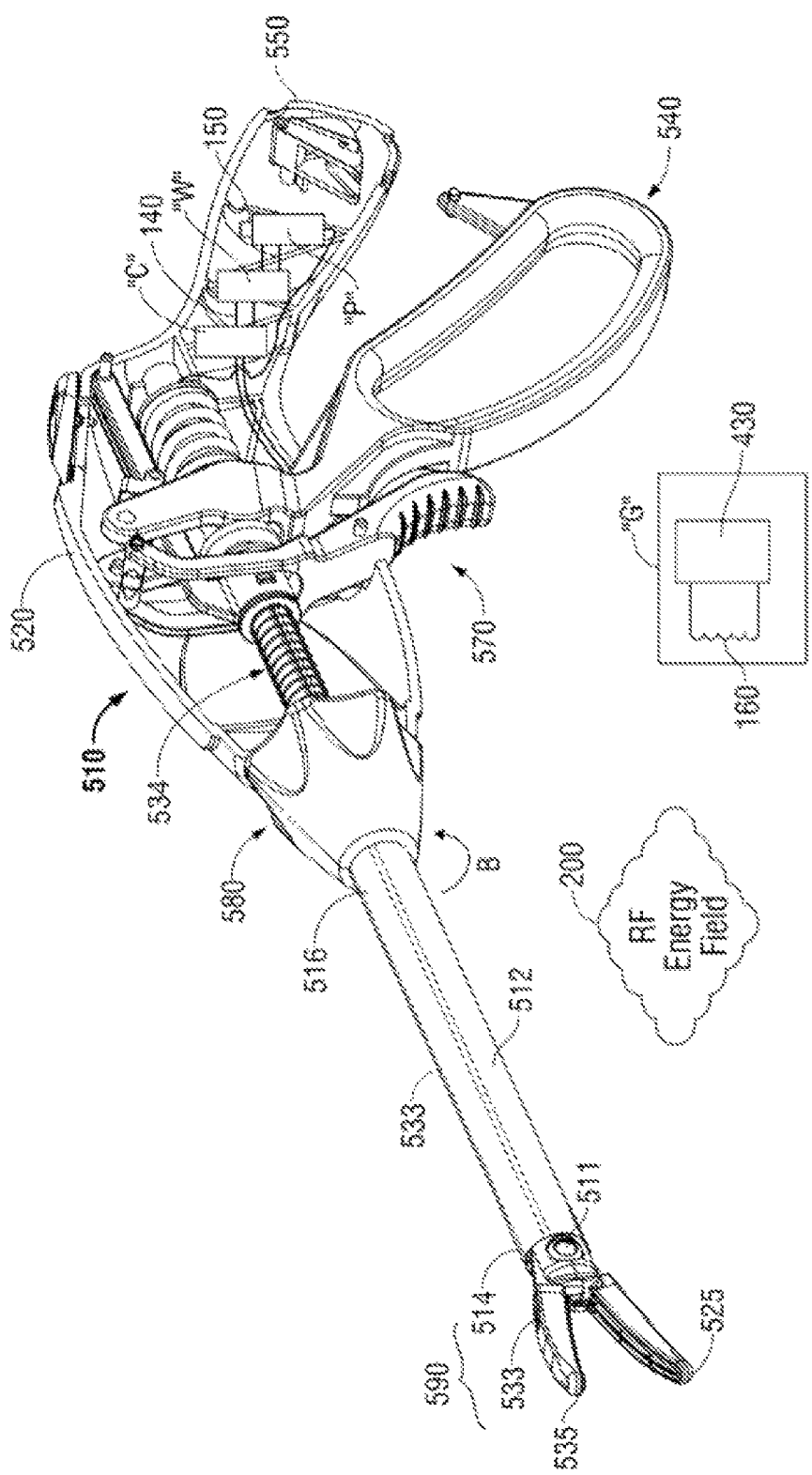
FIG. 5B is interior perspective view of the endoscopic forceps of FIG. 5A according to the present disclosure.

With reference to FIGS. 5A and 5B, an illustrative embodiment of a wireless electrosurgical apparatus, e.g., a bipolar forceps 510 (forceps 510) is shown. Forceps 510 is wirelessly connected to electrosurgical generator "G" through RF field 200 for performing an electrosurgical procedure. The electrosurgical procedure may include sealing, cutting, cauterizing, coagulating, desiccating, and fulgurating tissue all of which may employ RF energy. The electrosurgical generator "G" may be configured for monopolar and/or bipolar modes of operation and may include or be in operative communication with a system (not shown) that may include one or more processors in operative communication with one or more control modules that are executable on the processor. The control module (not explicitly shown) may be configured to instruct one or more modules to transmit electrosurgical energy, which may be in the form of a wave or signal/pulse to the forceps 510.

Forceps 510 is shown configured for use with various electrosurgical procedures and generally includes a housing 520, a rotating assembly 580 and a trigger assembly 570. For a more detailed description of the rotating assembly 580, trigger assembly 570, reference is made to commonly-owned U.S. patent application Ser. No. 11/595,194 filed on Nov. 9, 2006, now U.S. Patent Publication No. 2007/0173814.

With continued reference to FIGS. 5A and 5B, forceps 510 includes a shaft 512 defining a longitudinal axis "A" that has a distal end 514 configured to mechanically engage an end effector assembly 590 operably associated with the forceps 510 and a proximal end 516 that mechanically engages the housing 520. In the drawings and in the descriptions that follow, the term "proximal," as is traditional, will refer to the end of the forceps 510 which is closer to the user, while the term "distal" will refer to the end that is farther from the user. Shaft 512 is rotatable by actuation of rotating assembly 580. For example, shaft 512 may be rotated in a direction "B" or opposite the direction "B".

Handle assembly 530 includes a fixed handle 550 and movable handle 540. In one particular embodiment, fixed handle 550 is integrally associated with housing 520 and handle 540 is movable relative to fixed handle 550 for effecting movement of one or more components, e.g., a drive wire 533, operably associated with a drive assembly 534 (FIG. 5B) via one or more suitable mechanical interfaces, e.g., a linkage interface, gear interface, or combination thereof.

Drive assembly 534 is in operative communication with handle assembly 530 (see FIGS. 5A and 5B) for imparting movement of one or both of a pair of jaw members 525, 535 of end effector assembly 590. The drive assembly 534 may include a compression spring (not shown) or a drive wire 533 to facilitate closing the jaw members 525 and 535. Drive wire 533 is configured such that proximal movement thereof causes the movable jaw member, e.g., jaw member 535, and operative components associated therewith, e.g., a seal plate 528, to "flex" or "bend" inwardly substantially across a length thereof toward the non-movable jaw member, e.g., jaw member 525. For example, jaw member 535 may "flex" or "bend" about a joint 511. With this purpose in mind, drive rod or wire 533 may be made from any suitable material and is proportioned to translate within the shaft 512. In the illustrated embodiments, drive wire 533 extends through the shaft 512 past the distal end 514, see FIG. 5A for example.

Figure 6:
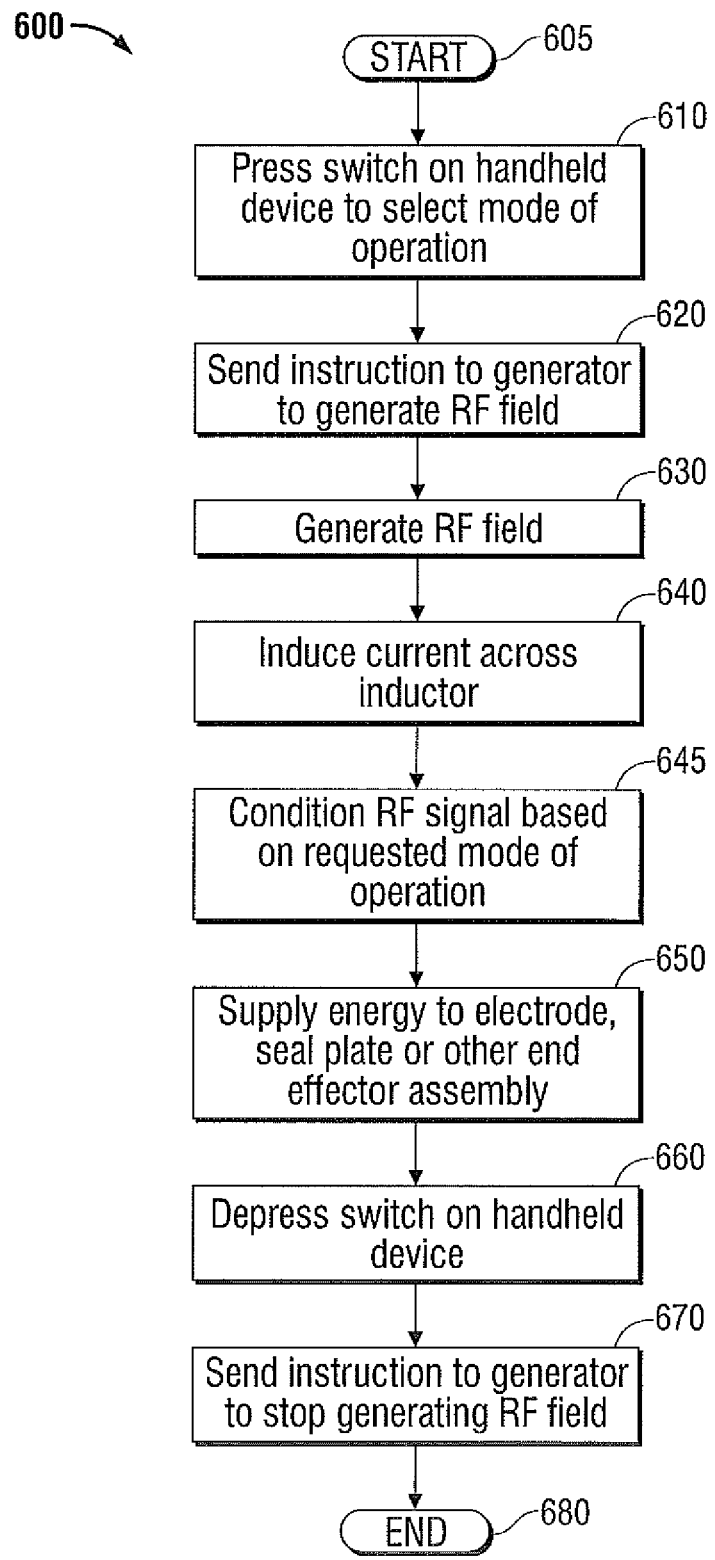
FIG. 6 is a flow chart of a wireless RF system according to the present disclosure.

FIG. 6 is a flow diagram of process 600 for operating a device, such as 100 or 510, within a wireless RF system. The process 600 starts at step 605, with an operator pressing a switch, such as 124a-124c or 571, on the handheld device 100 or 510 to select a mode of operation at step 610. An instruction specifying the mode of operation is sent to the generator "G" from the wireless communication board "W" to generate the RF energy field 200 according to the specified mode of operation at step 620. The generator "G" generates the RF field at step 630 using inductor 160. The RF field 200 induces, in step 640, a current to flow across inductor 150. The power board "P" conditions the RF signal produced from inductor 150 based on the requested operational mode at step 645. The power board "P" then supplies the RF signal to the electrode, seal plate, or other end effector assembly at step 650. When the operator completes the procedure, the operator depresses the switch, such as 124a-124c or 571, on the hand held device at step 660. The process ends at step 680, when the generator "G" receives and executes an instruction sent from the wireless communication board "W" instructing the generator "G" to stop generating the RF field 200 at step 670.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A method for wirelessly operating a hand held electrosurgical device, comprising;
 selecting a switch on the hand held electrosurgical device;
 sending an instruction wirelessly to a generator to generate an RF energy field;
 generating the RF energy field;
 inducing, by the RF energy field, a current across an inductor within the hand held device that causes an RF signal;
 charging a capacitor within the device; and
 supplying the RF signal to an end effector assembly to perform a surgical procedure.

2. The method of claim 1, wherein selecting the switch further comprises selecting a mode of operation for the device.

3. The method of claim 2, wherein the mode is cut, ablate, coagulate or seal.

4. The method of claim 2, further comprising:
 conditioning the RF signal into the selected mode.

5. The method of claim 4, wherein the selected mode is seal and the RF signal is conditioned into a pulsed waveform.

6. The method of claim 4, wherein the selected mode is cut and the RF signal is conditioned into a sinusoidal waveform.

7. The method of claim 1, wherein the device is a pencil or a forceps.

8. The method of claim 1, further comprising charging a rechargeable battery within the device.

9. A method for wirelessly operating a hand held electrosurgical device, comprising:
 generating an RF energy field;
 selecting a switch on the device to select a mode of operation;
 inducing, by the RF energy field, a current across an inductor within the device that causes an RF signal;
 charging a capacitor within the device;
 conditioning the RF signal into the selected mode; and
 supplying the conditioned RF signal to an end effector assembly to perform a surgical procedure.

10. The method of claim 9, wherein the mode is cut, ablate, coagulate or seal.

11. The method of claim 9, wherein the device is a pencil or a forceps.

12. The method of claim 9, further comprising charging a rechargeable battery within the device.

* * * * *